United States Patent [19]

Manoury et al.

[11] Patent Number: 5,001,132
[45] Date of Patent: Mar. 19, 1991

[54] PHENYLOXYPROPANOLAMINE DERIVATIVES AND THEIR APPLICATION IN THERAPEUTICS

[75] Inventors: Philippe Manoury, Verrières-le-Buisson; Jean Binet, Fontaine les Dijon; Gerard Defosse, Paris, all of France

[73] Assignee: Synthelabo, Paris, France

[21] Appl. No.: 432,686

[22] Filed: Nov. 7, 1989

[30] Foreign Application Priority Data

Nov. 8, 1988 [FR] France .................... 88 14538

[51] Int. Cl.$^5$ .................... A61K 31/44; C07D 247/02
[52] U.S. Cl. .................... 514/300; 546/121
[58] Field of Search .................... 514/300; 546/121

[56] References Cited

U.S. PATENT DOCUMENTS 4,234,595 11/1980 Kreighbaum et al. ............ 514/415

FOREIGN PATENT DOCUMENTS 0006614 1/1980 European Pat. Off. .
2463765 2/1981 France .
60-233074 11/1985 Japan .................... 546/121

Primary Examiner—Mary C. Lee
Assistant Examiner—Jacqueline Haley
Attorney, Agent, or Firm—Fleit, Jacobson, Cohn, Price, Holman & Stern

[57] ABSTRACT

Phenyloxypropanolamine derivatives in the form of racemates or enantiometers, of formula (I)

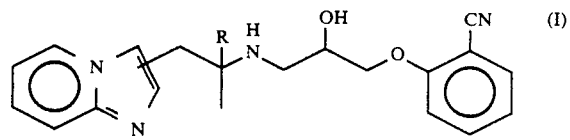

in which R is H or CH3, and their pharmaceutically acceptable salts.

3 Claims, No Drawings

PHENYLOXYPROPANOLAMINE DERIVATIVES AND THEIR APPLICATION IN THERAPEUTICS

The present invention relates to phenyloxypropanolamine derivatives, their preparation and their application in therapeutics.

The compounds of the invention correspond to the formula (I)

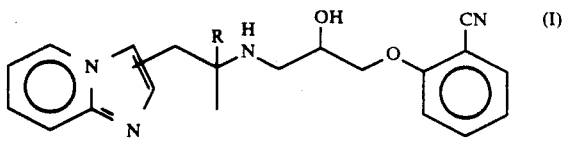

where R is H or $CH_3$ and may be in the form of pure enantiomers or racemates.

The addition salts of the compounds with pharmaceutically acceptable acids are comprised in the invention.

According to the invention, compounds (I) can be prepared according to the reaction scheme of the annex. The compound (II) is reacted with compound (III) in a solvent such as ethanol at reflux temperature.

The following examples illustrate the invention.

The analyses and IR and MNR spectra confirm the structure of the compounds.

Example 1

1-(2-cyanophenoxy)-3-[[2-(imidazo[1,2-a]pyridin-3-yl)-1-methylethyl]amino]propan-2-ol.

1.1. 3-(2-nitro-1-propenyl)-imidazo[1,2-a]pyridine.

10 g of imidazo[1,2-a]pyridine-3-carboxaldehyde is heated under reflux for 30 minutes with 3.6 g of ammonium acetate, 8 ml of acetic acid and 15 ml of nitroethane. The mixture is cooled, filtered, washed with water and dried. MP=225° C. (recrystallized from nitromethane).

1.2. 3-(2-nitro-1-propenyl)-imidazo[1,2-a]pyridine.

To 9 g of the previous derivative, suspended in 250 ml of a 50/50 mixture of dioxan-ethanol, 21 g of $NaBH_4$ are added by fractions. The mixture is shaked for ½ hour, and the solution evaporated. The residue is dissolved in water, 3.5 ml of acetic acid are added and the mixture is extracted with methylene chloride. The extract is washed with water, dried, filtered and evaporated. The product is purified by chromatography.

1.3. α-methyl (imidazo[1,2-a]-pyridin-3-yl)ethanamine. In a Parr apparatus, 6.7 g (0.033 mole) of the previous nitro-derivative dissolved in 125 ml of ethanol are hydrogenated in the presence of 5 g of Raney's nickel. The catalyst is filtered and evaporated to dryness. The hydrochloride is prepared in ethanol. MP>300° C.

1.4. 1-(2-cyanophenoxy)-3-[[2-(imidazo[1,2-a]pyridin-3-yl)-1-methylethyl]amino]propan-2-ol.

To a suspension of 4.3 g (0,0173 mole) of the previous compound in 13 ml of ethanol, 6.9 ml of 5.05 N sodium methylate are added ; the mixture is stirred for 5 min and 3.4 g (0.02 mole) of 1(2-cyanophenoxy)-2,3-epoxy-propane are added and then heated under reflux for 30 min. The solution is evaporated to dryness, dissolved in methylene chloride, washed with water, dried, filtered and evaporated. The compound is purified by chromatography and the fumarate prepared in acetone. MP=126° C.

EXAMPLE 2

1-(2-cyanophenoxy)-3-[[2-(imidazo[1,2-a]pyridin-2-yl)-1-methylethyl]amino]propane-2-ol.

2.1. 2-[2-(imidazo[1,2-a]-pyridin-2 yl)-1-methylethyl]-1H-isoindole-1,3-dione.

To a solution of 15.3 g (0.136 mole) of 2-aminopyridine in 80 ml of HMPT are added 25.3 g (0.08 mole) of 2-[(4-bromo-3-oxo-1-methyl) propyl]-1H-isoindole-1,3-dione. The solution is stirred for 5 h, poured into water, extracted from ether. The ethereal phase is washed with water, dried, filtered and evaporated. The hydrochloride is prepared in ethanol. MP=147° C.

2.2. α-methyl(imidazo[1,2-a]pyridin-2-yl)-ethanamine. 24 g (0.07 mole) of the above compound are heated under reflux for 3 h in 240 ml of 6 N HCl. The mixture is evaporated to dryness, dissolved in 5 N sodium hydroxide. The resulting solution is extracted with methylene chloride. The methylene chloride solution is dried, filtered and evaporated. BP =165° C. under 0.04 mm Hg.

2.3. 1-(2-cyanophenoxy)-3-[[2-(imidazo[1,2-a]pyridin-2-yl)-1-methyl-ethyl]amino]propan-2-ol.

1.75 g (0.01 mole) of the above amine in the form of the base are heated for about 1 h under reflux with 1.8 g (0.01 mole) of 1-(2-cyano-phenoxy)-2,3-epoxy-propane in 10 ml of ethanol. The solvent is evaporated. The residual oil is purified by chromatography. The maleate is prepared in ethanol MP=172° C. (recrystallized from methanol).

EXAMPLE 3

1-(2-cyanophenoxy)-3-[[2-(imidazo[1,2-a]pyridin-3-yl)-1,1-dimethyl-ethyl]amino]propan-2-ol.

3.1. 3-(2-nitro-2-methyl-1-propyl)-imidazo[1,2-a]pyridine. 144 g (0.44 mole) of (imidazo[1,2-a]pyridin-3-yl)-trimethylmethanammoniummethanammonium iodide (J. G. Lombardino J. Org. Chem. 30. 2403–7, 1965) are heated under reflux for 16 h with 48.5 ml (0.53 mole) of 2-nitropropane and 90 ml of 5.04 N sodium methylate.

The mixture is evaporated to dryness. The resulting residue is suspended in water and is filtered. The filtrate is then dissolved in 3 volumes of water : a colored gum precipitates and crystallizes.

After chromatographic purification on a silica column, the product is obtained. MP=131° C.

3.2. α,α-dimethyl-(imidazo[1,2-a]pyridin-3-yl)-ethanamine.

According to the same method as that described in 1.3. and from 12.7 g (0.058 mole) of the previous derivative, the product is obtained in the hydrochloride form. MP>300° C.

3.3. 1-(2-cyanophenoxy)-3-[[2-(imidazo[1,2-a]pyridin-3-yl)-1-dimethYl-ethyl]amino]propan-2-ol.

6.9 g (0.0365 mole) of the previous product are heated under reflux with 7.6 g (0.043 mole) of 1-(2-cyanophenoxy)-2,3-epoxy-propane in 40 ml of ethanol. The solvent is evaporated and the product is obtained by chromatography. The fumarate is prepared in ethanol. MP=206° C.

The compounds (I) prepared according to the process of the invention are represented, as examples, in the following table:

TABLE

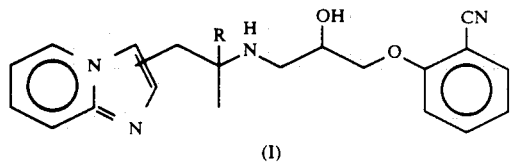

(I)

| Compound | R | bound | salt | MP (°C.) |
|---|---|---|---|---|
| 1 | H | 3 position | fumarate | 126 |
| 2 | H | 2 position | maleate | 172 |
| 3 | CH₃ | 3 position | fumarate | 206 |

The compounds (I) of the invention have been studied in a series of pharmacological tests which have demonstrated their interesting properties in the cardiovascular field. They have been particularly tested for their antiglaucoma activity.

The one-day acute intraocular pressure (IOP) response in normotensive and hypertensive eyes of monkeys has been evaluated according to the following test : intraocular pressure (IOP) was determined using an Alcon Pneumatonograph after light corneal anesthesia with proparacaine. After every IOP measurement, residual anesthetic was washed out with saline. After a baseline IOP measurement, test article or vehicle was administered in two 25 microliter aliquots to both eyes of 6 cynomolgus monkeys. Subsequent IOP measurements were taken at 1,3 and 7 hours after dosing. The right eyes of all monkeys had been given laser trabeculoplasty several months prior to this experiment, and developed ocular hypertension in the lasered eye. Animals were trained to sit in restraint chairs and conditioned to accept the pressure measurements.

The results are given in the following table:(see following page)

TABLE 2

| Intraocular Pressure Response in Cynomolgus Monkeys | | | | | |
|---|---|---|---|---|---|
| | | | Percent Change from Baseline | | |
| | | | 1hr | 3hr | 7 hr |
| Compound | Dose/eye | Eye | after dosage | | |
| ex. 1 | 500 μg | OD | −18.7 | −19.7 | −10.5 |
| | | OS | −2.7 | −3.1 | −6.8 |
| ex. 3* | 500 μg | OD | −26.7 | −23.1 | −15.1 |
| | | OS | −4.2 | −0.7 | −1.8 |
| ex. 3* | 500 μg | OD | −23.6 | −28.5 | −5.4 |

TABLE 2-continued

| Intraocular Pressure Response in Cynomolgus Monkeys | | | | | |
|---|---|---|---|---|---|
| | | | Percent Change from Baseline | | |
| | | | 1hr | 3hr | 7 hr |
| Compound | Dose/eye | Eye | after dosage | | |
| | | OS | −5.0 | −7.6 | −3.1 |

Notes
OD lasered; OS normal. N = 6. All compounds formulated as solutions or suspensions in a vehicle.
*Study repeated using different animals.

The compounds of the invention may be used for the treatment of the glaucoma.

They can be administered in a pharmaceutically acceptable excipient in an appropriate form:solutions or suspensions in a vehicle.

Annex

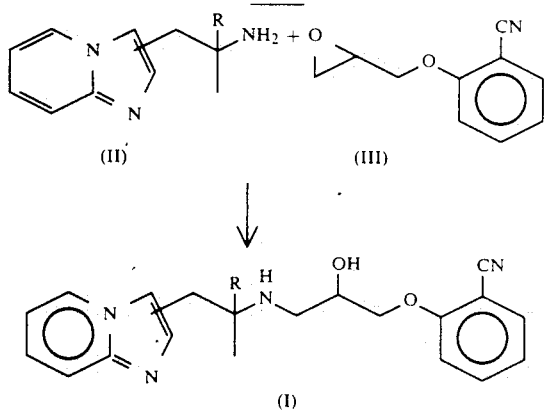

We claim:
1. Phenyloxypropanolamine derivatives in the form of racemates or enantiomers, of formula (i)

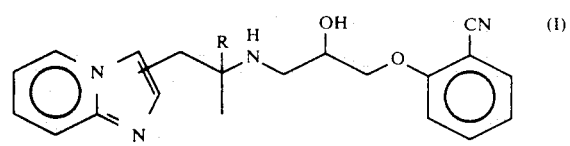

in which R is H or CH₃, or their pharmaceutically acceptable salts.

2. A pharmaceutical composition which comprises a pharmaceutically effective amount of a compound according to claim 1 and a pharmaceutically acceptable excipient.

3. A method of treatment of glaucoma which comprises administering to a subject an effective amount of a compound according to claim 1.

* * * * *